(12) United States Patent  
Maget et al.

(10) Patent No.: US 7,681,809 B2
(45) Date of Patent: Mar. 23, 2010

(54) ELECTROCHEMICAL DISPENSER

(75) Inventors: Henri J. R. Maget, La Jolla, CA (US); James Dikeman, El Cajon, CA (US)

(73) Assignee: M&R Consulting Services, San Diego, CA (US)

( * ) Notice: Subject to any disclaimer, the term of this patent is extended or adjusted under 35 U.S.C. 154(b) by 0 days.

(21) Appl. No.: 12/137,715

(22) Filed: Jun. 12, 2008

(65) Prior Publication Data

US 2008/0308647 A1    Dec. 18, 2008

Related U.S. Application Data

(60) Provisional application No. 60/943,755, filed on Jun. 13, 2007.

(51) Int. Cl.
*B05B 9/00* (2006.01)
(52) U.S. Cl. .................... 239/326; 239/34; 239/53; 239/57; 239/309; 239/327; 239/373; 222/95; 222/187; 222/386.5
(58) Field of Classification Search ............... 239/34, 239/53, 55, 56, 57, 309, 326, 327, 328, 373, 239/128, 135; 222/95, 187, 386.5
See application file for complete search history.

(56) References Cited

U.S. PATENT DOCUMENTS

| 3,876,115 | A | * | 4/1975 | Venus et al. ............... 222/183 |
| 3,981,415 | A | * | 9/1976 | Fowler et al. ............... 222/95 |
| 4,341,348 | A | * | 7/1982 | Dearling ................... 239/34 |
| 4,776,499 | A | * | 10/1988 | Magid ................... 222/386.5 |
| 4,902,278 | A | | 2/1990 | Maget |
| 5,427,870 | A | * | 6/1995 | Joshi et al. ................ 429/27 |
| 5,445,462 | A | * | 8/1995 | Johnson et al. ............ 401/132 |
| 5,681,435 | A | | 10/1997 | Joshi |
| 5,785,688 | A | | 7/1998 | Joshi |
| 5,899,381 | A | | 5/1999 | Gordon |
| 5,928,194 | A | | 7/1999 | Maget |
| 5,932,204 | A | * | 8/1999 | Joshi ................... 424/76.1 |
| 5,938,640 | A | | 8/1999 | Maget |
| 5,954,268 | A | | 9/1999 | Joshi |
| 5,968,325 | A | * | 10/1999 | Oloman et al. ............ 204/230.5 |
| 6,010,317 | A | | 1/2000 | Maget |
| 6,045,055 | A | | 4/2000 | Joshi |

* cited by examiner

*Primary Examiner*—Steven J Ganey
(74) *Attorney, Agent, or Firm*—Frank G. Morkunas

(57) ABSTRACT

A device for achieving a controlled low emanation rate of small volumes of liquid solutions, such as single or multi-component solutions, fragrances, or pheromones, for pest and insect management or fragrance enhancement. The device has a housing with an upper chamber to hold a bladder containing desired liquid solution to be released, a lower chamber containing an electro-chemical gas generator, a collector pad for receiving liquid solution from the bladder, and a cap which, when translated downward, activated the gas generator which fills the upper chamber with gas exerting pressure on the bladder which in turn forces the liquid solution from the bladder onto the pad for release to the environment. The gas generator is capable of releasing gases such as hydrogen, oxygen, or carbon dioxide at extremely small, pre-determined, and adjustable rates.

32 Claims, 7 Drawing Sheets

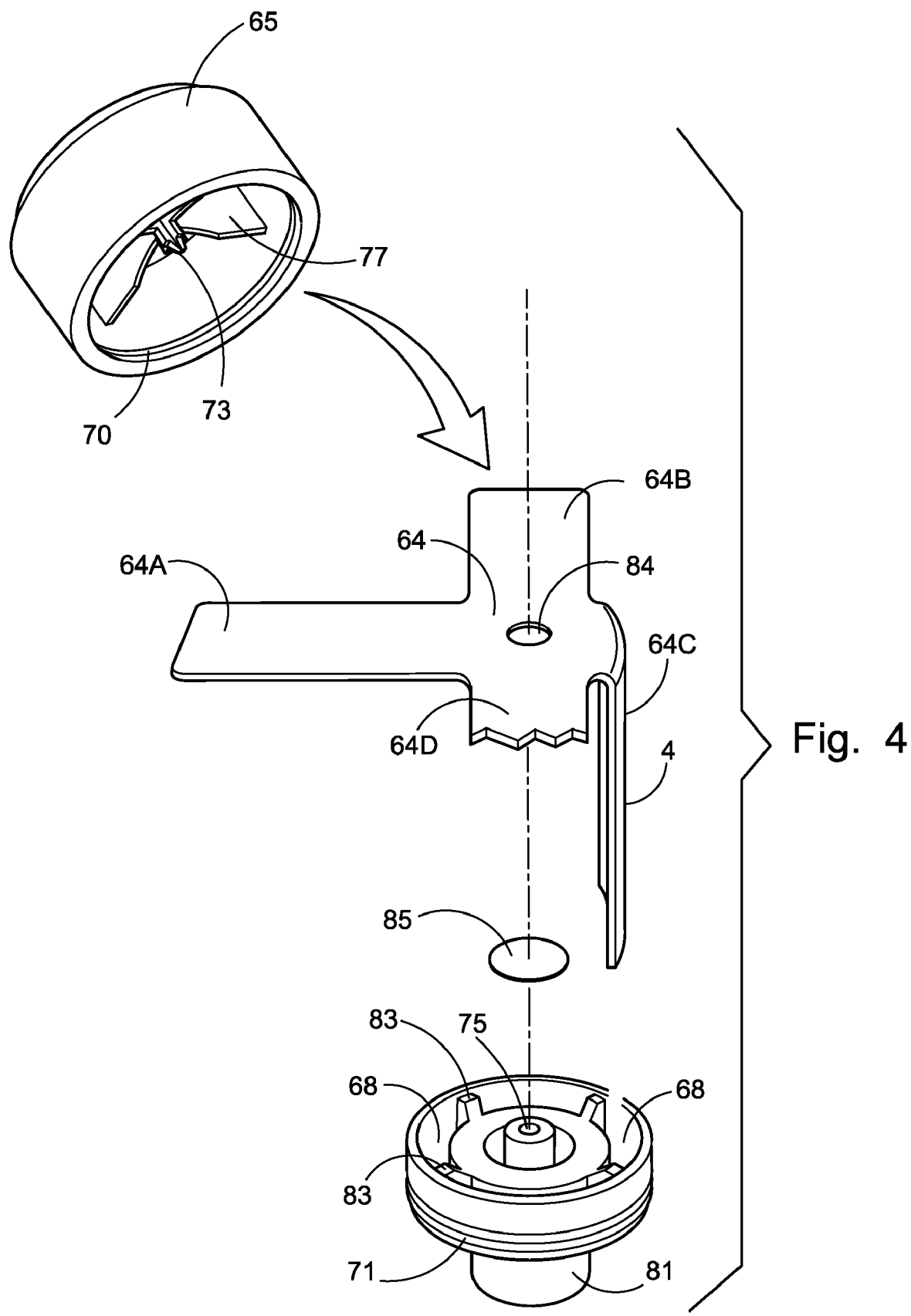

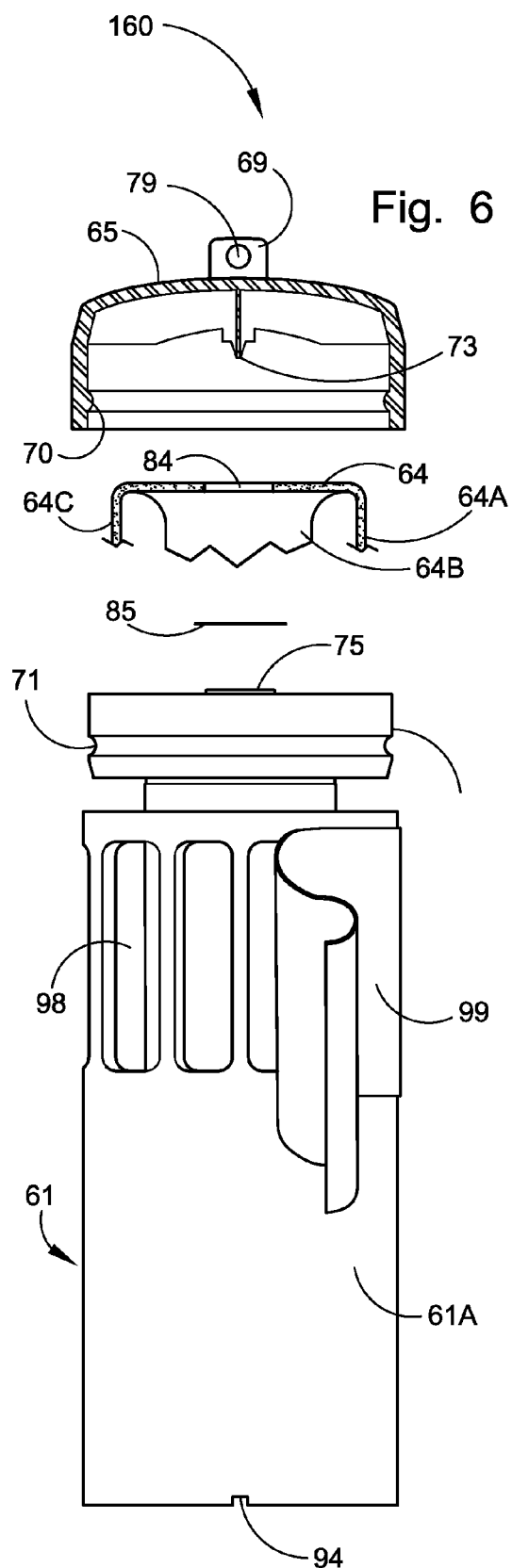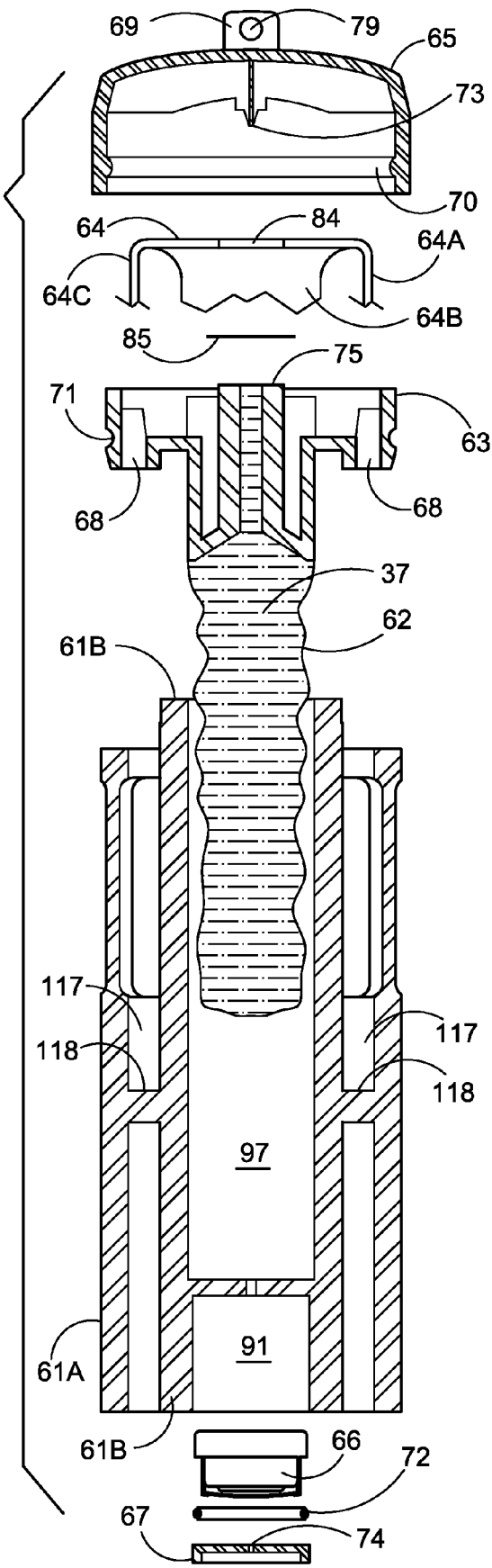

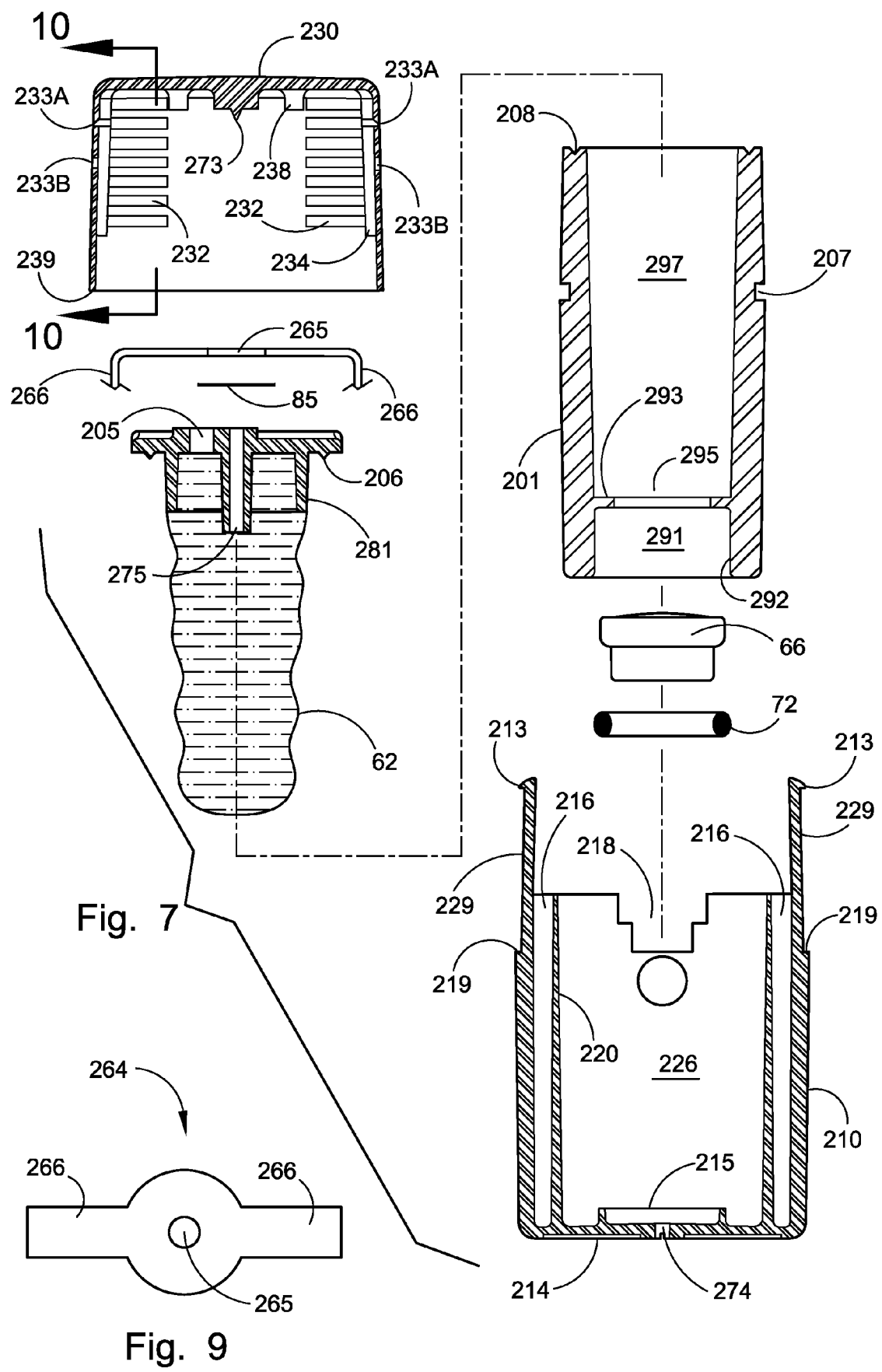

ELECTROCHEMICAL DISPENSER

CROSS REFERENCES TO RELATED APPLICATIONS

This application claims the benefit of U.S. Provisional Application No. 60/943,755, filed on Jun. 13, 2007.

STATEMENT REGARDING FEDERALLY-SPONSORED RESEARCH OR DEVELOPMENT

Applicant has received funding from the U.S. Department of Agriculture, Grant Number 2004-33610-15132.

BACKGROUND OF THE INVENTION

1. Field of the Invention

The invention herein relates to vapor release devices/dispensers. More particularly it relates to small portable dispensers to disperse vapors into the surrounding environment.

2. Description of the Prior Art

In recent years there have been numerous applications for small, easily portable liquid and other fluid dispensers. One use of these devices is to provide for dispersion of gases and vapors into the environment. Typical are devices used to alter environmental scents, such as in homes and offices. Another important application, used for a large range of environmental conditions, such as temperature and elevation, is for the release of pheromones. Pheromones are chemical substances released by insects for the purpose of communication.

Chemists have learned to reproduce these chemicals and entomologists have been successful in using them for the management of insects. Insect management requires the release, preferably at constant rates, of minute quantities of pheromones, generally less than 10 milligrams/day, over time periods of up to 12 months. The release of pheromones at these minute rates has been achieved mainly by diffusion of the pheromones through plastic materials, a process which is extremely temperature-sensitive and not field-reliable, since the rate also decreases with time and renders the releaser useless since a minimum threshold of pheromone concentration in the air is not maintained.

Pheromone dispensers have to be economical since in current uses as many as 500-1,000 devices are needed per hectare to control insects. The requirements of low cost, accuracy of delivery, duration of delivery, environmental conditions ranging from sub-freezing to desert-like summer temperatures, elevations from sea level to 10-15,000 feet, and in some instances re-usability, are stringent for practical dispensers.

Dispensers meeting some of these requirements have been described by Maget in U.S. Pat. No. 5,928,194 and Maget, et. al., in U.S. Pat. No. 6,383,165. An embodiment of the latter has been shown to be effective for the control of bark beetles, an insect responsible for the destruction of millions of acres of forest, worldwide. U.S. Pat. No. 6,383,165 is hereby incorporated by reference herein in its entirety, including the detailed description of the various devices used in the delivery of pheromones. In addition, my previously filed provisional application, 60/943,755, filed on Jun. 13, 2007, is also hereby incorporated by reference.

The current device described herein, and in my provisional application ['755], represents an improvement over the previous dispensers inasmuch as they are more economical to produce, easier to fill, include re-usable components, and yet achieve the same performance. Low cost, ease of storage and operation, including continuous delivery over long time periods, such as months, are features and capabilities necessary for commercial dispensers of fragrances as well as pheromones.

OBJECTS OF THE INVENTION

One object is to provide practical, low cost, commercial electrochemical fluid dispensers capable of releasing fluids in the environment under controlled conditions, whether for environmental control reasons or for aesthetic reasons; these fluids being either highly volatile or having low vapor pressures.

Another object is to show that by careful combination of the fluid pumping/release rates and fluid collection pad sizes and configuration, the fluid releaser system can be tailored to achieve, rapidly, steady state emission rates, even for multi-component fluid solutions.

A further object is to provide users with dispensers that are easy to fill, transportable and easy to start, even under field conditions, without the need for special tools or equipment.

The foregoing has outlined some of the more pertinent objects of the improved dispenser as set forth in this disclosure. These objects should be construed to be merely illustrative of some of the more prominent features and applications of the improved dispenser. Many other beneficial results can be attained by applying the disclosed improved dispenser in a different manner or by modifying the improved dispenser within the scope of the disclosure. Accordingly, other objects and a fuller understanding of the improved dispenser as set forth in this disclosure may be had by referring to the summary of the improved dispenser and the detailed description of the preferred embodiment in addition to the scope of the improved dispenser defined by the claims taken in conjunction with the accompanying drawings.

SUMMARY

The above-noted problems, among others, are overcome by the improved electrochemical fluid dispenser releasing vapors of chemicals or any liquid solutions into the environment at controlled low emanation rates of small, pre-determined and adjustable volumes of such chemicals or liquid solutions for environmental control or for aesthetic reasons such as, but not limited to, fragrance enhancers. The device has a housing with an upper chamber to hold a bladder containing desired liquid solution to be released, a lower chamber containing an electro-chemical gas generator, a collector pad for receiving liquid solution from the bladder, and a cap which, when translated downward, activates the gas generator which fills the upper chamber with gas exerting pressure on the bladder which in turn forces the liquid solution from the bladder onto the pad for release to the environment.

The gas generator is capable of releasing gases such as hydrogen, oxygen, or carbon dioxide at extremely small, pre-determined, and adjustable rates. The device allows the release of single or multi-component solutions, fragrances, and pheromones onto the collection pad from which it can emanate into the environment either directly or through one or more release vents in the cap or, is an embodiment having an outer wall to the housing, through release vents in the outer wall.

The invention achieves the results of my previous patent U.S. Pat. No. '165; however certain modifications and features have been incorporated to simplify filling, operation, and start-up. The cap is removable exposing a fill or exit port to the bladder. This makes the device reusable by filling the bladder with a desired liquid solution and replacing the gas generator.

Additionally, in one embodiment, gas pressure is applied directly to the fluid before releasing it to the collection pad, rather than using a barrier interface between the gas and the fluid. The pheromone, pheromone solution, or fragrance under pressure generated from the electrochemical gas source, is delivered, via a conduit, to a collection pad from which it can emanate (evaporate).

The present invention provides the necessary features to render the system operational and reliable under a variety of environmental conditions, while achieving constant release. More specifically, selection of a common solvent for all components of the fluid, thermal insulation, geometry of the fluid exit conduit and pad properties and sizes are needed to achieve the expected delivery profiles.

For complex fluid mixtures, that is for fluids containing more than two components, an algorithm is required to predict the minimum pad size and geometry, to achieve, as rapidly as possible, the steady-state emanation conditions.

The foregoing has outlined the more pertinent and important features of the various embodiments of the improved dispenser as set forth in this disclosure in order that the detailed description that follows may be better understood so the present contributions to the art may be more fully appreciated. Additional features of the improved dispenser will be described hereinafter which form the subject of the claims.

It should be appreciated by those skilled in the art that the conception and the disclosed specific embodiment may be readily utilized as a basis for modifying or designing other structures and methods for carrying out the same purposes of the improved dispenser as set forth in this disclosure. It also should be realized by those skilled in the art that such equivalent constructions and methods do not depart from the spirit and scope of the improved dispenser as set forth in the appended claims.

BRIEF DESCRIPTION OF THE DRAWINGS

For a fuller understanding of the nature and objects of the improved dispenser as set forth in this disclosure, reference should be had to the following detailed description taken in conjunction with the accompanying drawings in which:

FIG. 4 is a detailed exploded view of the head, cap, and pad configuration of the dispenser.

FIG. 5 is a partially exploded and partially cut-away view of a second embodiment of the dispenser.

FIG. 6 is a cut-away exploded view of the dispenser of FIG. 5.

FIG. 7 is a cut-away exploded front view of a third embodiment of the dispenser.

FIG. 9 is a detailed plan view of the pad for use with the dispenser of FIGS. 7 and 8.

DETAILED DESCRIPTION

General Description from Provisional Application

In this section, reference to FIGS. 1 through 6 relate to the figures associated with my provision application No. 60/943,755, filed on Jun. 13, 2007, and not to the figures associated with this current non-provisional application and are provided herein as a point of reference, support as necessary for this current non-provisional application, and for possible later submission of other non-provisional applications. Consequently, these figures are not reproduced herein but have been incorporated by reference above.

Figure 1:
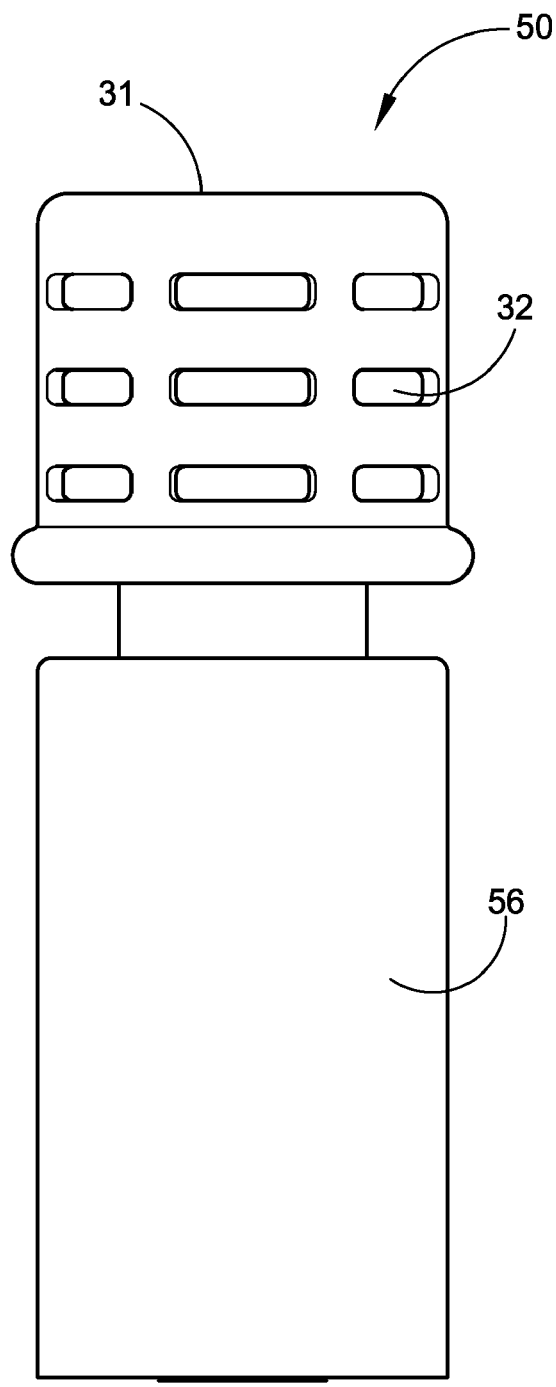
FIG. 1 is a side elevation view of one embodiment of the dispenser.

An elongated reservoir 1, in FIG. 1 of provisional application ['755], is located within a thermal insulation shroud 2. The reservoir, fitted with fluid evacuation tubing 3, holds a pheromone solution 4, by way of illustration. A releaser head 5 is securely attached to reservoir 1 by means of a threaded connector 20. A seal 6 is provided to prevent the leakage of gas around the threaded connector 20.

Releaser head 5 has two cavities; cavity 7 to hold gas generator 8 and cavity 9 to hold collection pad 10. Gas generator 8 is equipped with a seal 11 which prevents gas leakages to the environment. A metal connector 12 wraps around gas generator 8. Metal connector 12 closes the electrical circuit through resistor 13 that allows the current to flow through the circuit, once closed. On stand-by, ribbon 14 prevents electrical connector to close the circuit. By pulling ribbon 14 the circuit is closed and the generator is operative. The gas released by generator 8, supplied via conduit 15, applies pressure to the liquid in reservoir 1 and pushes fluid to collection pad 10 from which it can evaporate to the environment.

Figure 2:
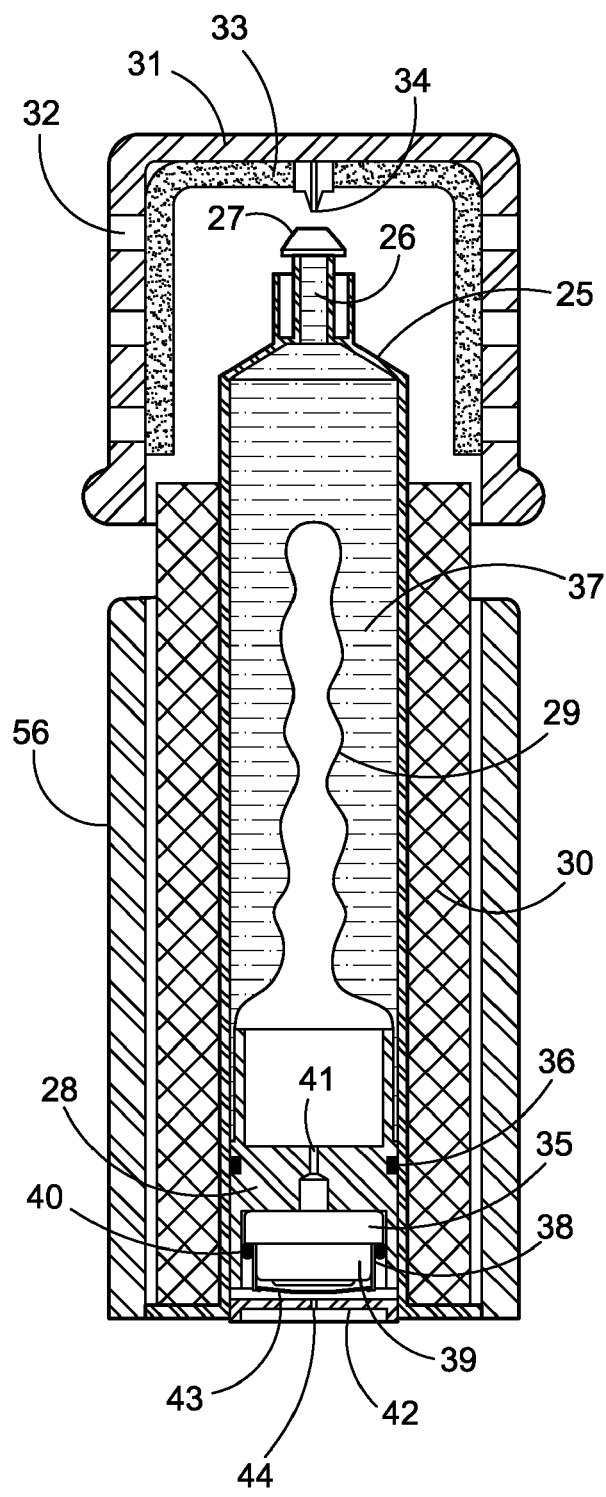
FIG. 2 is a cut-away view of the dispenser of FIG. 1.

FIG. 2 of provisional application ['755] represents a variance of the embodiment of FIG. 1 of provisional application ['755]; the gas generator is now located at right angle from the device axis to allow for the axial location of fluid evacuation tubing 3.

Whenever high emanation rates are required, or when the released fluid contains compounds with extremely low vapor pressures, the collector pad size becomes large and it cannot anymore be accommodated within the cross-sectional area of the dispenser.

Figure 3:
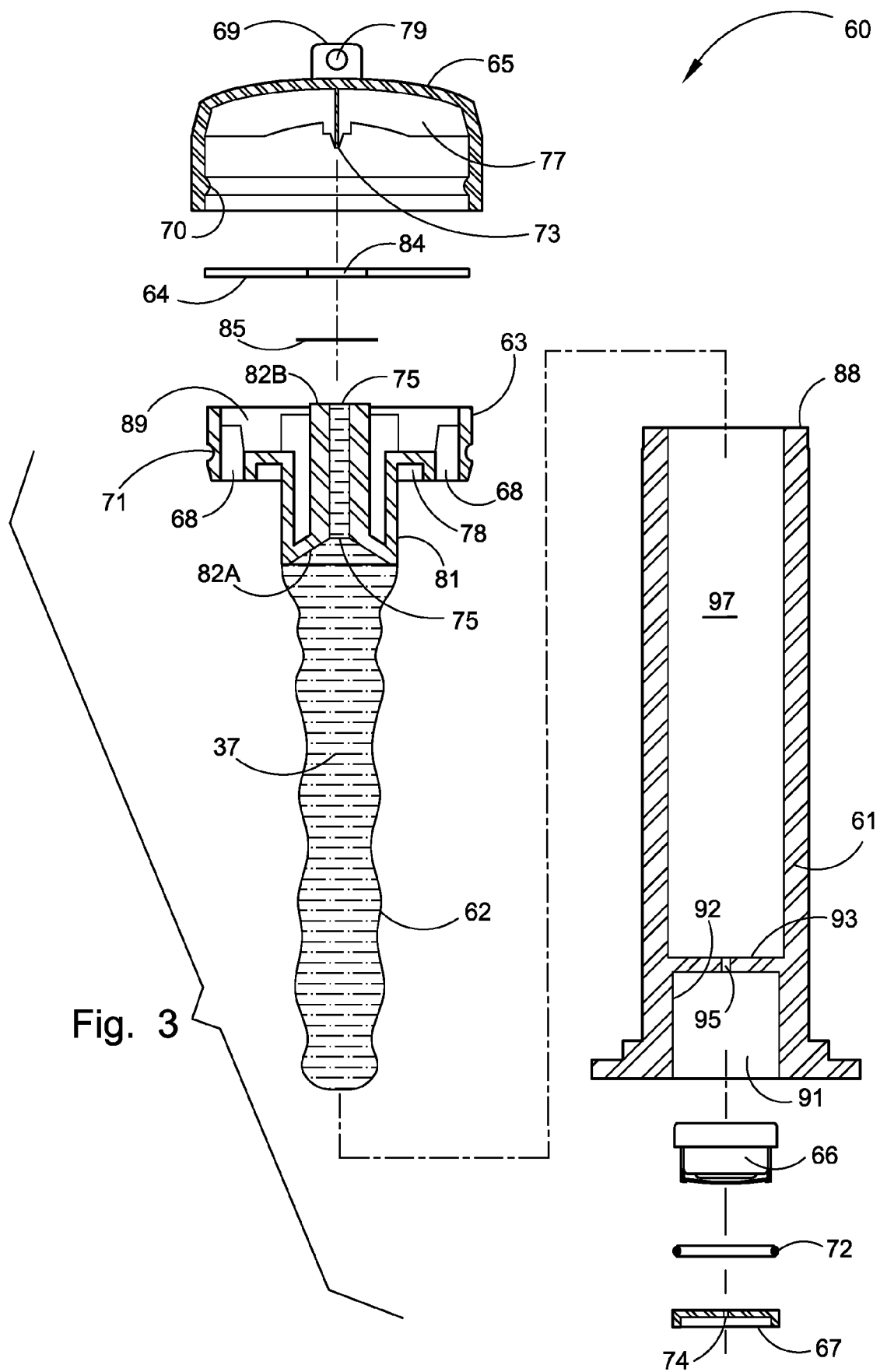
FIG. 3 is an exploded cut-away view of a preferred embodiment of the dispenser.

In this case, FIG. 3 of provisional application ['755] provides a solution by wrapping the pad around the dispenser. In FIG. 3 of provisional application ['755], plastic reservoir 1 is fitted with an adaptor 19, which also contains a section of fluid release tubing 3. Adaptor 19 is designed to mate with gas generator holder 17. Reservoir 1 is placed within an insulation shroud 2 that has a shoulder 2A and a section 2B with reduced diameter, designed to fit within releaser head 5 by sliding shroud 2 into head 5 until stopped by the shoulder 2A.

Releaser head 5 holds gas generator holder 17, collector pad 10, slot 24 and fluid exit channel 23 which, during assembly, is aligned with exit channel 23A within adaptor 19. The releaser head has vertical openings 21 to allow evaporation of the solution from the pad into the environment. During operation, the fluid leaving the reservoir through tubing 3 exits at 23A and eventually through conduit 23 onto collector pad 10.

The gas generator is located within holder 17. It has a seal 22 that prevents gas leakage once it is mated with adaptor 19. Lid 18 holds the gas generator connectors 12A and 12B, which, during operation, are in electrical contact with gas generator 8.

On stand-by, a flat insulating ribbon, not shown, placed between generator 8 and contact 12A, exits through slot 24. To start operation, the ribbon is pulled, and the spring action of connector 12A closes the electrical contact. The flat axially truncated dispenser geometry is employed to allow it to be attached to flat vertical surfaces.

A similar configuration is illustrated in FIG. 3A of provisional application ['755], albeit in this case some components are aligned in a different manner and the emanation slots are horizontal instead of vertical. FIG. 3B of provisional application ['755] represents another variance of releasers of FIGS. 1, 3 and 3A of provisional application ['755]. In this instance, the gas generator is sealed within an enclosure capped by an elastomeric push-button Start of operation is achieved by depressing the button.

The storage sub-system consists of the reservoir 1, the thermal insulation 2, the tubing 3 and the stored fluid 4. By separating the storage sub-system from the releaser head, it is possible to fill the reservoir by using conventional filling equipment and then attaching it to the releaser head. It also provides the option for the user to fill the dispenser at a selected site with a selected fluid. A similar two-part fluid dispenser is also described by Maget is U.S. Pat. No. 5,938, 640. A self-contained system, U.S. Pat. No. 6,045,055, describes a closed assembly delivering fluid to plug(s) for emanation. For reasons discussed in the following such a system would not deliver fluid at a constant rate, unless provisions described in this invention are provided.

The reservoir acts as a flexible bag or bladder. The material selected for its composition is judiciously selected for compatibility with the pheromone or fragrance solution, which includes mainly organic compounds which are excellent solvents. Glass, metals (steel, aluminum) and certain plastics are candidate materials. The optimum material for the bladder 62 and its intended purpose is a is a five-layer co-extruded barrier film produced by Dow Chemical referred to a Saranex.

Furthermore, the reservoir material has to be as impermeable as possible to the gas produced by the gas generator. Again glass, metals and specific plastics are acceptable. Judicious selection of the plastic materials is required lest gas losses through diffusion prevent reliable operation of the dispenser. Also the choice of materials is further limited by the need for processability to be able to produce the required reservoir shapes. Plastic materials which can be molded or thermoformed are required. These include materials such as Delrin, Nylon, Teflon, PET or rigid PVC. With verbenone, a practical pheromone, we have encountered many problems with incompatibility with polyvinylchloride (PVC) polymers and terephtalates.

The elongated geometry of the reservoir is also important. Since many pheromones are expensive, it is essential that maximum utilization be achieved. The reservoir geometry should be such that at least 95% of the fluid can be evacuated.

Although the gas generation rate is rather insensitive to temperature, cyclic daily temperature excursions have an impact on the expansion/contraction of the gas phase above the liquid. This expansion/contraction is proportional to the extreme daily temperatures divided by the absolute temperature, or $\Delta T/T$, where $\Delta T$ represents the maximum less minimum temperature and $T$ is the absolute initial temperature. For example, a 15° C. circadian upward excursion from a nominal temperature of 20° C. would result in an impact of (15/293.2) or 5.1% in the volume change. For a gas volume of 100 cc, this would represent an uncontrolled delivery of 5.1 mL of fluid due to thermal differences, only.

For a fluid evacuation conduit of less than 5.1 mL capacity, this would mean that on the down cycle (−15 C drop), the reservoir will "suck-in" air. This thermal siphon can have adverse effects over the long term whenever the chemicals in the solution are sensitive to oxidation. Another effect will be the uncontrolled nature of the fluid delivery, since thermal daily cycle vary with weather, seasons, and the like.

To alleviate thermal excursion, the reservoir should be insulated to, as a minimum, dampen the thermal excursion range. However, this solution will only reduce the magnitude of the thermal cycle.

The insulation material and external shroud also provide protection from natural or artificial light to prevent UV-induced breakdown of the solution chemicals. Furthermore, the insulation provides protection from breakage of the glass reservoir, if such reservoir material has to be used.

To prevent air bubbles intake, an appropriate design of the conduit is important. The minimum conduit volume can be estimated from the worst case situation, that is the reservoir is filled with gas. From the previous example it should be at least 5.1 mL.

The shape of the conduit should also consider the need to achieve fluid delivery continuum, if at all possible. This need will be further explored in the following discussion of fluid receiver pads. To achieve a delivery as continuous as possible, the linear fluid displacement should be maximized to result in a steady stream of fluid. A capillary conduit end 3A, as illustrated in FIG. 1 of provisional application ['755] should be selected., since extremely small fluid delivery rates, i.e., about 5-10 microliters/hour are contemplated for the dispensers in question. In that instance a capillary with an inside diameter of 0.05 cm would be appropriate. It would result in a linear fluid displacement rate of 2.5-5 cm/hr, pushing the fluid towards the receiver pad. [Note: the linear displacement rate (L/t) in cm/hr is obtained from the following equation: $L/t(cm/hr)=(4/pi)(R/D^2)$ where R is the liquid flow rate in mL/hr and D is the inside diameter of the capillary in cm].

Furthermore, to be able to evacuate mostly all of the fluid in the reservoir, as expected whenever expensive chemicals are being dispensed, it is important to provide the conduit with a geometry 3B, as illustrated in FIG. 1, which allows nearly all the liquid to be extracted at the time of near delivery completion. [Note: some pheromones cost as much as $ 1,000/gram].

The insulation has another function, namely preventing UV radiation to reach the reservoir contents. Pheromones are complex, often unsaturated, organic molecules susceptible to UV-induced oxidative degradation, which would result in the inactivation of the semiochemical.

The releaser head includes means to attach the head to the reservoir sub-system, such as a screw-on interface 20, the gas generation sub-system and the fluid collector. Economical gas generators are generally electrochemical cells, which are also compact and energy-efficient.

The gas generators can be divided into two types: generators needing an access port to the environment and self-contained generators without need to access the environment.

Generators of the first type include:
  a. oxygen concentrators requiring air intake to generate enriched oxygen as described by Maget in U.S. Pat. No. 4,522,698;
  b. electrolytic decomposition of organic acids into carbon dioxide and hydrogen, whenever one gas has to be rejected to the environment, as described by Maget in U.S. Pat. No. 6,413,238 and a co-pending application;
  c. water electrolysis producing oxygen and hydrogen, whenever one gas has to be rejected.

Generators of the second type include:
  a. gas cells, producing only hydrogen as a gas, as described by Winsel in U.S. Pat. No. 5,242,565;
  b. electrolytic decomposition of organic acids producing and utilizing both generated gases, $CO_2$ and $H_2$ as described by Maget in U.S. Pat. No. '238;
  c. electrolysis of water, when both gases $O_2$ and $H_2$ can be used.

The selection of either of these electrochemical generation means is dependent on the chemical nature of the solution to be delivered. For example, many organic compounds or solutions are sensitive to degradation by oxygen, and therefore oxygen or oxygen-containing gases are not recommended. Hydrogen is mostly inactive but difficult to contain and $H_2$ losses through members of the dispenser can result in uncontrolled fluid delivery. $CO_2$ is generally inert to organic molecules and easy to contain.

In most instances, the gas generator is driven by DC energy supplied from a small battery, hearing-aid cell or button cell. In few instances, such as for $H_2$ gas cells, the reaction between chemicals contained in the cell produces DC electric energy and a gas by-product. These gas cells do not require an auxiliary battery.

The gas generation rates vary from 0.23 to 1.35 cc gas NTP/hour per milli-ampere, depending on the selected electrochemical process. Since small battery storage capacities do not generally exceed 200 mAhr, it will be apparent that these generators are capable to deliver only small quantities of fluids, generally not exceeding 250 mL, unless designed with the capability for battery replacement.

There are, however, lower limits of gas generation and fluid delivery rates. They are considered to be about 5 microliters/hour, corresponding to cell currents of 4 to 25 microamps. Below these limits, thermal effects and diffusional losses become too significant to maintain control of the fluid delivery. These limits will have an impact on the composition of the fluid to be delivered. For example, pheromones are often delivered at rates of 1-2 milligrams/day, or about 1-2 microliters/day, or about 1% of the controllable delivery rates of the gas generator-driven dispensers. Therefore, to achieve this extremely low delivery schedule, the pheromone needs to be diluted in an appropriate inactive solvent.

Channel 15 providing the gas to the reservoir is a narrow circular conduit adequate for gas transfer at low rates, but yet preventing liquid from the reservoir to splash onto the gas generator which, in some instances, could affect the generator performance.

Orifice 16, through which the start ribbon passes, also serves as an inlet air port for oxygen enrichment generators, or as a gas exit port for undesirable gas generator gases such as hydrogen or oxygen.

It should be apparent that judicious selection of the gas generator is dependent on many variables and factors, such as environmental conditions, liquid composition, selection of the gas generator and design of the dispenser. This decision process will also have to include means to release the fluid into the environment.

The fluid, released as a result of gas pressure exercised on the solution, is captured by a collection pad. The pad, made of natural or synthetic fibers, is available commercially from sources such as Waterman Corp. For additional protection of the pad from the environment, a water repellant layer of Tyvek (a DuPont product) is placed on the external side of the collector pad. The Tyvek layer will protect the pad from water, dust, etc.

Although precise delivery of the solution is a necessary step to achieve reliable release, emanation of the pheromone(s) or fragrances from the collector pad is another critical step. Pad selection can not be casual for reasons presented in the following.

For a multi-component pheromone solution, the rate of accumulation of the solution on the collector (dW/dt) results from the delivery rate of the fluid to the pad (R) less the evaporation rate. This relationship can be expressed symbolically by:

$$(dW/dt) = R - \{[E/a\delta\rho_f(t)]\Sigma x_i(t) P_i\}(W)$$

where:

(W) is the weight (mg) of fluid on the pad at any time; R is the fluid delivery rate, in mg/hr; (a) is the retention coefficient of the pad (volume of fluid/volume of pad); $\rho_f$ is the fluid density in the pad; δ is the pad thickness; ($x_i$) is the species (i) mole fraction in the liquid phase in the collector; $P_i$ is the vapor pressure, in mm Hg, of the pure component (i); (E) is the specific evaporation rate from the collector in mg/hr-cm$^2$-mmHg and (t) is the time in hours.

The value of (E) will depend on the environmental conditions such as wind velocity. Since the wetted area (A) in cm$^2$, on the pad equals $W/a\rho_f\delta$, it will be possible to determine the minimum pad area necessary to achieve a constant release rate from the pad.

Dispenser release rate stability is achieved when (dW/dt)=0; i.e., the emanation rate is identical to the fluid release rate. Analytical solutions of the previous equation are possible only for pure components and binary solutions. To solve the equation for solutions containing more then two components it is necessary to resort to computer finite element analysis.

We have developed such models and compared the results with experimental measurements. They have allowed us to select optimum pad properties and solution compositions to achieve pre-set requirements such as the daily release rates of individual components from a multi-component solution. Moreover, they have allowed us to release multiple pheromones from a single solution, whereas the art to this date consists of using one releaser for each individual component.

High vapor pressure semiochemicals, a rare occurrence, require small collection pad areas of a few cm$^2$, while most semiochemicals, displaying vapor pressures of less than 0.01 mmHg, require pad sizes of 15-20 cm$^2$, even for components delivered at rates of a few milligrams/day. Similarly, fragrances consisting of a multiplicity of organic chemicals may evaporate singularly in an unpredictable manner unless adequate fluid dispersion throughout the pad is achieved in a timely fashion and the pad is of adequate size.

Whenever gas and liquid are incompatible, because of possible chemical interaction, a barrier (thin plastic film) can be placed between gas and fluid. Such a device is described in Maget's U.S. Pat. No. 4,902,278 for a two-dimensional planar fluid delivery pump, and again in Maget, et. al., U.S. Pat. No. 6,383,165. Additionally, the film barrier also prevents fluid vapors to contact the gas generator.

DETAILED DESCRIPTION OF THE PREFERRED EMBODIMENTS OF THIS NON-PROVISIONAL APPLICATION

The benefits described above and in my provisional application ['755] are incorporated in one preferred embodiment of the dispenser 50 as illustrated in FIGS. 1 and 2 [FIG. 7 of my provisional application ['755]]. This dispenser 50 requires only one gas seal and renders the dispenser orientation-insensitive, a feature of importance for transportation. A reservoir 25, such as a plastic syringe, with a conventional exit port 26 is capped by syringe cap 27. The distal end of the syringe 25 is fitted with an adaptor 28, which contains the gas generation module 35.

Adaptor 28 is fitted with seals 36 to prevent liquid from escaping reservoir syringe 25, and with a collapsible thin-walled plastic bag/bladder 29, designed to hold the gas generated by generator module 35. Reservoir 25 is surrounded by insulation 30 to dampen any large environmental circadian temperature variations within fluid 37 in fluid reservoir syringe 25. As described earlier such fluids include, but are not limited to, pheromones or fragrance solutions.

The lower part of the dispenser 50 is further placed within a shroud or housing 56 that provides protection from any external physical damage. The upper part of the dispenser 50 is covered by cap 31, fitted with vent slots 32, fluid collection pad 33, and pin 34. During the filling cycle syringe cap 27 is removed, and then put back into the sealing position. The dispenser 50 can be freely transported without spills. At the time of use, cap 31 is pushed downward, pin 34 penetrates the cap 31 to allow fluid to escape to be collected by pad 33 from which it can evaporate. The gas generator start-up operation is also the result of downward pressure applied to the cell module 38, which promotes electrical contact between the battery 39 and the electro-chemical gas generator 35.

In this illustration the electro-chemical gas generator 35 produces oxygen as the motive gas. This form of electro-chemical gas generator 35 has been previously described by Maget, et. al., in U.S. Pat. No. 6,010,317. This electrochemical gas generator 35 comprises an electrochemical cell module 38 and a battery 39. The electrochemical gas generator 35 is located in the adaptor 28, where a seal 40 is provided to prevent gas losses. A contact strip 43 is connected to the battery terminal. The complete gas generation unit is sealed by means of friction plate 42 and is provided with an air intake port 44. On stand-by the plate 42 is kept away from contact strip 43. The generator is started by pushing plate 42 upward, thereby allowing contact between the contact strip 43 and the cell module 38. The electrochemical gas generator 35 becomes operational and produces gas. The gas produced passes through the air exit port 41 and is captured in and by the expandable bag/bladder 29. As the bag/bladder 29 inflates it pushes fluid 37 out of the reservoir syringe 25 and up to the collection pad 33.

In this embodiment the most critical component is the bag/bladder 29 which expands under generated gas pressure. The bag/bladder 29 should be relatively resistant to gas transmission or else gas losses therefrom would affect fluid delivery rates. Most plastic films designed for food preservation will be adequate, particularly films such as Saranex, available from Dow Chemicals Co.

FIGS. 3 and 4 [FIGS. 8A and 8B of provisional application ['755]] illustrate a first preferred dispenser 60 for volatile compounds. The releaser body 61 in this embodiment has an upper chamber 97 and a lower chamber 91 adjacent to the bottom of the body 61. The upper chamber 97 and the lower chamber are separated by a chamber ledge 93 which has a gas exit port 95 therethrough.

A reservoir head 63 has a centrally located downward extending collar 81 and an outer wall with a groove 71 around the outer wall. A slot 78 around the bottom of the reservoir head 63 adjacent to the collar 81 seats over and secures to the top 88 of the body 61. The collar 81 has a fluid exit port 75 therethrough extending from the bottom 82A of the collar 81 to its top 82B. The top 82B is approximately on the same horizontal plane as the outer wall of the reservoir head 63. An inner chamber 89 is defined between the outer wall and the collar 81. The bottom 82A of the collar 81 is approximately concave in configuration.

One or more slots 68 separated by head fins 83 reside between the outer wall of the reservoir head 63 and the bottom slot 78. FIG. 4 more clearly illustrates the slots 68 showing four. Before the reservoir head 63 is secured to the body 61, the bladder 62 is heat-sealed to the collar 81 as best illustrated in FIG. 3. The bladder 62 is filled with suitable fluid 37 for the intended purpose. The fluid exit port 75 is sealed with a suitable sealing member 85 to prevent undesired evaporation or loss of the fluid 37 within the bladder 62. An absorption pad 64 is placed over the reservoir head 63 and seal 85 covering the inner chamber 89.

The reservoir cap 65 is placed over the reservoir head 63 in such fashion that the protruding inner shoulder 70 around the inner surface of the side wall of the reservoir cap 65 removably seats into the groove 71 of the reservoir head 63. As so seated, the downward extending approximately centrally located spike 73 on the underside of the top of the reservoir head 63 does not touch or penetrate the seal 85.

A plurality of axially displaced support members 77 extend outward from the spike 73 to the inner surface of the side wall of the reservoir cap 65. The support members 77 provide structural support for the spike 73 and stabilize the pad 64 after the seal 85 is pierced by the spike 73.

As previously described, the collar 81 of the reservoir head 63 holds the thin film plastic bag/bladder reservoir 62 which is heat-sealed to the collar 81 which extends downward from the reservoir head 63. The reservoir head 63 is ultrasonically welded and heat-sealed to the reservoir body 61 which typically is tubular in shape. The pad 64 rests on top of the reservoir head 63. This pad 64 typically may be circular in configuration. A central port 84 in the pad 64 allows for fluid 37 contained within the reservoir bag/bladder 62 to be released therefrom and onto the pad 64. On the outside top of the reservoir cap 65 is a tab 69 having an aperture 79 therethrough.

For the dispenser 60 to properly function, the characteristics of the bladder 62 are such that it has an extremely low fluid/liquid diffusion rate and is impermeable to gas penetration.

A typical material for the bladder is a heat-sealing thin film bag produced by Dow Chemical and referred to as Saranex which is a five-layer co-extruded barrier film. The composition of the collar 81 requires that it be made compatible plastic materials to accommodate the sealing of the bag 62 in a air-tight leak-free union. Generally the collar will be of a polyethylene composition and the bag will have a polyethylene layer such that each have virtually identical softening temperatures to make the leak-free air-tight seal between bag and collar.

The reservoir cap 65 firmly, but removably, secures on top of the reservoir head 63 as described above. The reservoir cap 65 has multiple functions, the primary of which are to protect the pad 64 from the elements after the seal 85 is pierced, to securely attach the reservoir cap 65 to the reservoir body 61 by means of an internal shoulder or ridge 70 which fits against the groove 71 on the outer perimeter of the reservoir head 63 surface, and to provide means to suspend the dispenser 60 on an external object through an aperture 79 on the wing or tab 69 on the top of the reservoir cap 65.

An electrochemical gas generator 66 is seated into the bottom chamber 91 of the dispenser 60. A ledge 93 with an aperture 95 therethrough maintains the electrochemical gas generator 66 in place and separates the electrochemical gas generator 66 from the reservoir bag/bladder 62. The electrochemical gas generator 66 also is fitted with a circular seal or O-ring 72 which ensures a gas tight contact with the bottom chamber wall 92 at the distal end of the tubular body 61. Finally, a chamber cap 67, with a small central port 74, is placed tightly over the electrochemical gas generator 66 sealing the chamber 91 and preventing the electrochemical gas generator 66 from dislodging from the dispenser 60.

A typical generator 66 envisioned here is an electrochemical oxygen generator, producing pure oxygen from air, using a nested cell having a gas generator and battery to power the gas generator, as described by Maget et al, in U.S. Pat. No. 6,010,317. The dispenser 60 is filled via the fluid exit port 75 which is then sealed and protected from unintended release by means of a heat staked thin seal 85 such as, but not limited to, aluminized foil.

Reservoir cap 65 as engaged onto reservoir head 63 by means of the shoulder 70 and groove 71 alignment, places the dispenser 60 on stand-by. At time of use, the reservoir cap 65 is firmly pressed onto the reservoir head 63 which pushes the shoulder 70 out of the groove 71 and downward. This action will cause the spike 73, an integral part of the reservoir cap 65, to pierce the seal 85 to allow fluid 37 to be pumped to the pad 64 surface once the electrochemical gas generator 66 is engaged. The generator 66 is engaged by pushing the chamber cap 67 into the lower chamber 91 provided at the bottom of the body 61 where the electro-chemical gas generator 66 resides. This starts the pumping action.

This action results in two important effects; internal electrical contact within the nested cell to initiate electrical contact to the electrochemical gas generator 66 which generates gas. The o-ring seal 72 around the electrochemical gas generator 66 prevents the gas from flowing downward and out the air intake port 74 which serves to "feed" air to the gas generator 66. The only direction the generated gas may escape is through the gas exit port 95 and into the upper chamber 97.

As the gas builds up in the upper chamber, the pressure exerted by the gas on the bladder 62 causes the ejection of small pre-determined quantities of fluid 37 from the reservoir bag/bladder 62 and onto the pad 64. The amount of fluid so ejected is determined by the amount of gas being generated by the electrochemical gas generator 66. This amount may be adjusted as desired. Fluid evaporation from the pad 64 and out of the dispenser 60 takes place through the slots 68 provided in the reservoir head 63.

After all the fluid 37 is ejected, the dispenser may be refilled with fluid 37. To accomplish this, the reservoir cap 65 is removed from the reservoir head 63 exposing the fluid exit port 75. The bladder 62 is replenished via the fluid exit port 75 in the collar 81. The fluid exit port 75 acts not only as the fluid release port when gas is being generated, but also acts as the fluid fill port as necessary.

FIGS. 4 through 6 [FIGS. 9A and 9B of provisional application ['755]] illustrate a dispenser 160 for fluids with low vapor pressure requiring larger evaporation surfaces than dispenser 60 can accommodate by its configuration. This dispenser 160 is similar to that illustrated in FIGS. 3 and 4, as described above, except for the body 61, also generally tubular in configuration, consists of an outer wall 61A and an inner wall 61B bridged together internally by means of a bridge 118, thus creating an annular cavity 117 which can now hold a large surface area pad 64 having four extended wings 64A-D as illustrated in FIG. 4. This pad 64 with wings 64A-D is inserted into the annular cavity 117 through the slots 68 provided in the reservoir head 63.

The top of the outer body 61A is provided with side vents 98 that allow for free air motion over the complete pad surface from the top center of the pad 64 and out over the respective wings 64A-D and out the side vents 98. These side vents 98 provide for greater diffusion if they are vertically disposed as illustrated in FIG. 5. The slots 68 in the reservoir head 63 align with the side vents 98 in the outer wall 61A after the pad 64 is placed thereon and its wings 64A-D set down through the slots 68 and the reservoir cap 65 inserted over the outer wall 61A.

In this embodiment, the bottom slots 68 of the reservoir head 63 seat over the top of the inner wall 61B. The bridge 118 between the inner wall 61B and the outer wall 61A prevent fluid 37 from escaping from any area except from the side vents 98. The snap-activation described for the previously described dispenser 60 is the same for this dispenser 160. The reservoir cap 65 is pushed down causing the spike 73 therein to pierce the seal 85. The electro-chemical gas generator 66 is activated causing generated gas to enter the upper chamber 97 and exert pressure on the embedded bladder 62 forcing the fluid 37 therefrom and onto the pad 64, 64A-D.

Additionally, the annular cavity 117 is also designed to become a well for the pumped fluid. For example, since the pumping action of the electro-chemical gas generator 66 releases fluid in a continuous manner, an offset in evaporation rate (such as a reduction possibly due lower temporary temperatures) may result in excess fluid delivered to the pad 64, beyond the pad's fluid storage capacity. The excess fluid will be stored in the annular cavity 117, held in place by the annular bridge 118 between the outer wall 61A and the inner wall 61B and from there re-supply the pad 64 with fluid as the normal environmental conditions are reestablished.

This embodiment is designed for higher-volume release and, because of such, primarily for use outdoors. To protect this dispenser 160 from the elements, particularly rain, a protective water-repellent film 99 covers the side vents 98. A typical film for this purpose is Dupont's Tyvek® family of protective barriers and films. The film 99 prevents water from penetrating into the dispenser 160 yet allows free 'breathing' of the film 99 so as not to adversely affect the operation of the dispenser 160.

FIGS. 7 through 10 [FIGS. 10A through 10D of my provisional application ['755]] illustrate a variance of the previously described dispensers 60, 160. In this embodiment, the dispenser 200 is more user-friendly. For example, the dispenser 200 is on stand-by and is prevented from being accidentally snapped together by use of a removable outer shell "peel-away" pull tab or lock 217. When the lock 217 is removed, a simple vertical compression action of the cap 230 simultaneously allows the sealing foil 85 to be pierced and the generator 66 to be snapped into place and activated thereby causing the gas generation and pumping action to begin in similar fashion as previously described for dispensers 60, 160; a single phase snap-action.

Figure 8:
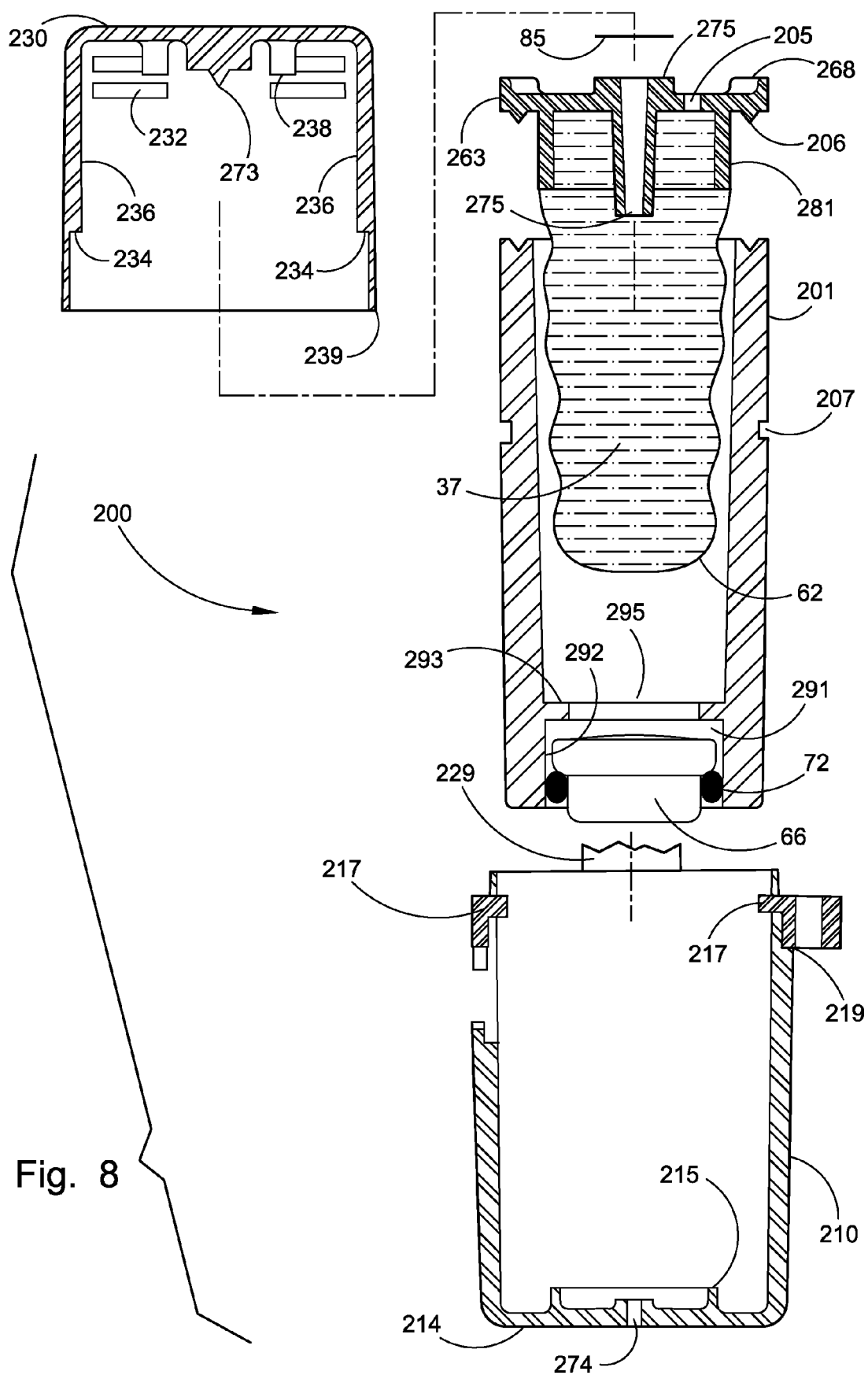
FIG. 8 is a cut-away exploded side view of a third embodiment of the dispenser.

FIGS. 7 and 8 represent a cross-section of the dispenser 200 in front elevation view and side elevation view, respectively. The dispenser 200 has a housing 210 with an inner wall 220 on each side on the housing 210 thereby defining a side space or side chamber 216 on each side of the housing 210 and a central space in between and within the inner walls 220. Extending upward on each side of the housing 210 is an elongated tab 229 having a width-W3 and an outward protruding stop member 213 on its top. Downward of the stop member 213, the elongated tab 229 terminates at a step 219 on the outside surface of the housing 210.

On the inside bottom 214 of the housing 210 is an annular ring 215 having a pre-determined diameter-W1. Approximately centrally located within the annular ring 215 is an air intake port 274.

An inner body 201 seats into the central space or chamber 226. The inner body 201 has outer groove 207, a chamber ledge 293 near to its bottom defining an upper chamber 297 above the chamber ledge 293 and a lower chamber 291 below the chamber ledge 293. The lower chamber 291 has a diameter-W2 which is slightly larger than diameter-W1. This configuration permits the inner body 201 to slide downward such that the lower chamber 291 nests around the annular ring 215.

A gas exit port 295 in on the chamber ledge 293 which forms a pathway between the upper chamber 297 and the lower chamber 291. Much like the previously described dispenser's 60, 160 mode of operation, an electrochemical gas generator 66, with o-ring seal 72 abutting the lower chamber walls 292 in gas-sealing fashion, will be in and sealed within the lower chamber 291 but not activated.

A reservoir head 263 is fitted with an reservoir bladder 62 around its collar 281 in similar fashion as previously described for dispensers 60, 160. Unlike the previously described dispensers 60, 160, the reservoir head 263 has a fluid exit port 275 and a separate fluid fill port 205. The function of the fluid exit port 275 is as described previously, to permit the release of fluid 37 within the reservoir bladder 62 to escape when the seal 85 is breached and the electro-chemical gas generator 66 is pumping gas into the upper chamber 297.

The reservoir head 263 also has an upstanding ridge or wall 268 for supporting the pad 264 to be placed therein or thereon. The seal 85 is placed between the pad 264 and the fluid exit port 275 to prevent premature evaporation or loss of fluid 37. The wings 266 of the pad 264 insert over the reservoir head 263 and downward into the respective side chambers 216. An aperture 265 in the pad 264 facilitates release of the fluid 37 in the reservoir bladder 62. An energy director 206 under the ridge 268 and adjacent to the collar 281 function to facilitate the ultrasonic welding of the reservoir head 263 onto the inner body 201.

The inner body 201 and the reservoir head 263 are ultrasonically welded together using this, typically annular, energy director 206 as a guide and facilitator. This sealing of the inner body 201 to the reservoir head 263 is done after the reservoir bladder 62 has been attached to the collar 281 in similar fashion as previously described for dispensers 60, 160. The reservoir bladder 62 is filled with fluid 37 through the fluid fill port 205 after which both the fluid fill port 205 and the fluid exit port 207 are sealed on top by a heat staked seal 85; preferably a metalized plastic film.

Topping off this dispenser 200 and switching it from operational to non-operational mode is the cap 230. The unique structure of the cap 230 serves to activate and de-activate the dispenser 200, to support the pad 264 with a plurality of pad supports 238 on the inside top of the cap 230 protruding downward, and to permit evaporating fluid to escape from the dispenser 200 by way of the vents 232. In between the pad supports 238, and approximately centrally located inside the ceiling of the cap is a spike 273 which, when the cap 230 is pushed downward, pierces the seal 85, activates the electro-chemical gas generator 66, and begins the operation.

Figure 10:
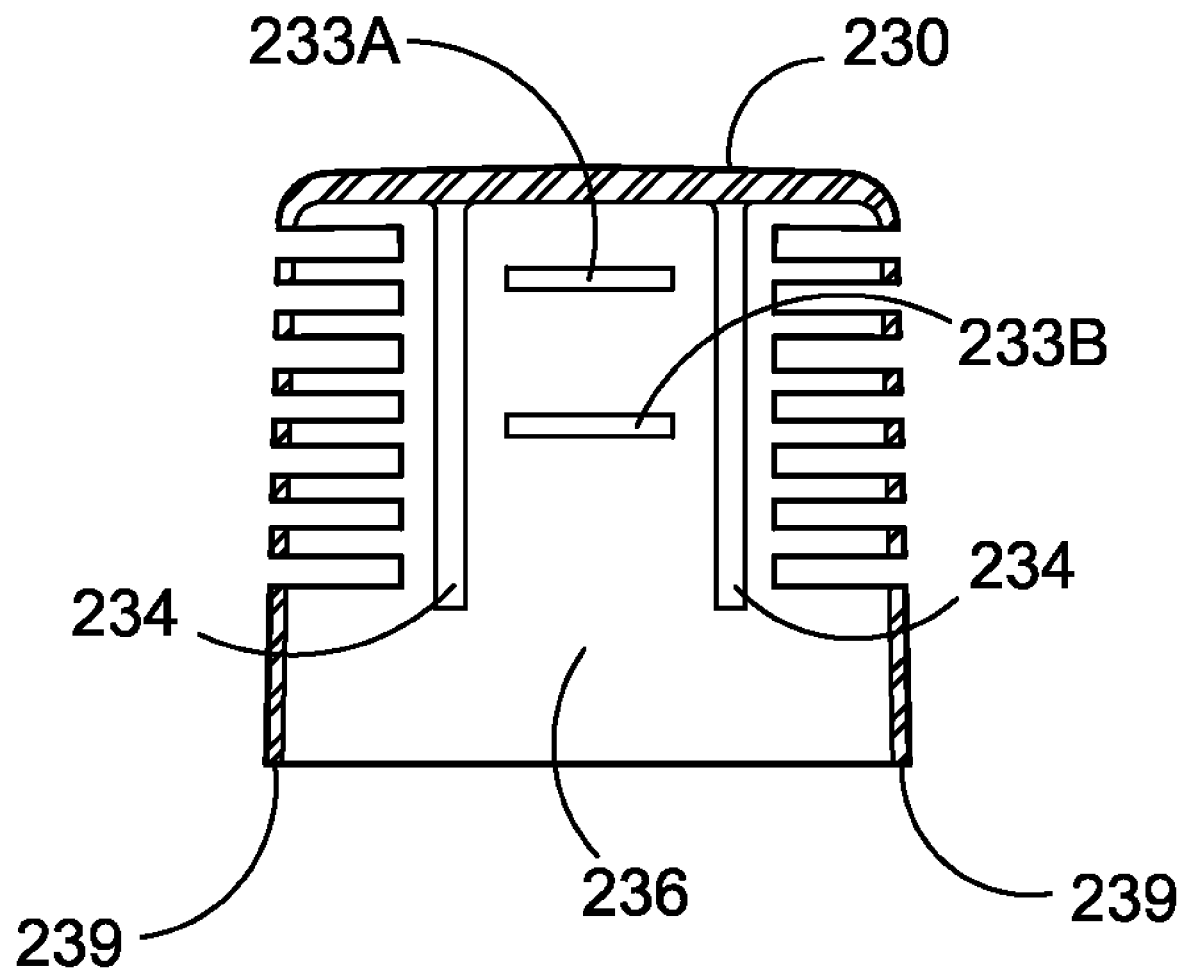
FIG. 10, as taken on line 10-10 of FIG. 7, is a cross section side view of the cap for use with the dispenser of FIGS. 7 and 8.

Referring in particular to FIG. 10, on each inner side wall of the cap 230 is a registration slot 236 having a width-W4 as defined by two vertically disposed inward protruding guides 234. On the registration slot 236 are at least two horizontally disposed catches 233A, the upper catch, and 233B, the lower catch. These catches 233A, 233B register with the stops 213 on each side of the elongated tab 229. Width-W3 of the elongated tab 229 is slightly less than width-W4 of the registration slot 236 thereby permitting the tabs 229 to translate up and down within the registration slot 236.

In stand-by mode, the stops 213 of the dispenser 230 are seated into catches 233B wherein the bottom 239 of the cap 230 is above the step 219 on the housing 210. In this position a gap 218 is defined from the bottom of the cap 230 and the cut-out on the housing 210. A retaining tab or lock 217 seats through the gap 218 and into the groove 207 around the inner body 201 to prevent pre-mature activation of the dispenser 200.

To activate the dispenser 200 for the first time, the lock 217 is removed from the groove 207; this will permit the user to initiate the push down, snap-action, on the cap 230. Until the lock 217 is removed the cap 230 cannot be pushed downward. Once so removed, the cap 230 is pushed downward to pierce the seal 85 and activate the electro-chemical gas generator 66. Typically, the cap 230 is pushed downward such that the bottom 239 of the cap 230 rests on the step 219 of the housing 210 and also, typically, the stops 213 align with the upper catches 233A. To deactivate the dispenser 200, one need only to pinch the sides of the cap 230 and pull upward. The pinching action eases the pressure exerted by the stops 213 on the upper catches 233A permitting their release and movement of the stops 213 to the lower catches 233B. This action can stop an electro-chemical gas generator 66 capable of being stopped from generating gas which in turn stops the pressure build up in the upper chamber 297 which forces the fluid 37 from the reservoir bladder 62.

We claim:

1. A device for dispensing fluids automatically comprising:
   (a) a base housing having a top surface, a bottom, an upper chamber within said base housing, a lower chamber within said base housing below said upper chamber, a chamber ledge extending fully across the base housing and separating said upper chamber from said lower chamber wherein said chamber ledge has a gas exit port, and a removably insertable chamber cap on the bottom of said base housing covering said lower chamber;
   (b) a removably insertable reservoir head having a head top, a head bottom, a circular head wall between said head top and said head bottom and perpendicularly disposed to said head top and said head bottom, with a groove therearound, a collar extending downward from said head bottom having a collar bottom with a fluid exit port from said collar bottom through said head top, an inner chamber above said head bottom between said outer wall and said collar, and a bottom slot on said head bottom adjacent to said collar and completely encircling said head bottom, wherein said bottom slot seats onto and into the top of and completely around said base housing;
   (c) a bladder on said collar for holding fluid therein, said bladder comprised of a flexible material which is substantially gas impermeable and liquid impermeable;
   (d) a pad in said reservoir head above said collar and within said inner chamber;
   (e) a reservoir cap having a closed top, a side wall extending downward from said closed top, and an open bottom, wherein a shoulder protrudes inward from said side wall and is in closing communication with said groove; and
   (g) electro-chemical gas generating means for generating gas, said gas generating means contained and sealed within said lower chamber such that as gas is generated said gas cannot escape from said lower chamber except through said gas exit port and into said upper chamber; whereby as said chamber cap is pressed into said lower chamber, said electro-chemical gas generating means is activated generating gas into said upper chamber forcing fluid out of said bladder onto said pad.

2. The dispenser of claim 1 further comprising an air intake port through said chamber cap.

3. The dispenser of claim 1 further comprising a pad aperture in said pad, said pad aperture in communication with said fluid exit port.

4. The dispenser of claim 1 further comprising a seal over said fluid exit port.

5. The dispenser of claim 1 wherein said reservoir cap further comprises a cap tab on top of and outside of said closed top, said cap top further comprising a cap tab aperture.

6. The dispenser of claim 1 wherein said reservoir cap further comprises a centrally located spike under said closed top and protruding downward toward said open bottom and a plurality of vertical support members under said closed top extending from said spike outward to said side wall.

7. The dispenser of claim 1 further comprising a plurality of slots through said reservoir head between said head wall and said bottom slot.

8. The dispenser of claim 1 wherein said collar bottom is concave.

9. The dispenser of claim 1 wherein said bladder is heat-sealed to said collar.

10. The dispenser of claim 1 wherein said collar and said bladder are comprised of a polyethylene composition with each having approximately identical softening temperatures to create an approximate leak-free air-tight seal between said collar and said bladder.

11. The dispenser of claim 1 wherein said bottom slot of said reservoir head is ultrasonically sealed to said top of said base housing.

12. The dispenser of claim 1 further comprising an outer wall around said base housing attached to said base housing by a bridge completely around and outward of said base housing and around and inward of said outer wall.

13. The dispenser of claim 12 further comprising an annular cavity above said bridge.

14. The dispenser of claim 13 further comprising a plurality of vertically disposed side vents on the outer wall in communication with said annular cavity.

15. The dispenser of claim 14 further comprising a removably attachable protective cover over said side vents.

16. The dispenser of claim 15 wherein said protective cover comprises a water-resistant breathable material.

17. The dispenser of claim 12 wherein said reservoir head further comprises one or more reservoir head slots in communication with said inner chamber and wherein said pad further comprising a plurality of outward extending wings insertable through said reservoir head slots.

18. A device for dispensing fluids automatically comprising:
  (a) a base housing having a top surface, a bottom, a cut-out on said top surface, an inner side wall on each side of said base housing defining a central chamber and a side chamber on each side of said central chamber, and an annular ring on the bottom inside of said base housing;
  (b) an inner body having an upper chamber, a lower chamber, a chamber ledge extending fully around the inner body and separating said upper chamber from said lower chamber wherein said chamber ledge has a gas exit port and wherein said inner body seats down and around said annular ring;
  (b) a removably insertable reservoir head having a head top, a head bottom, an annular collar extending downward from said head bottom and perpendicularly disposed to said head bottom, and a fluid exit port within said collar;
  (c) a bladder on said collar for holding fluid therein, said bladder comprised of a flexible material which is substantially gas impermeable and liquid impermeable;
  (d) a pad in said reservoir head above said head top, said pad having a pad aperture in communication with said fluid exit port;
  (e) a reservoir cap having a top, a downward extending wall from said top defining an inner surface therein, and a plurality of vents on said downward extending wall; and
  (g) electro-chemical gas generating means for generating gas, said gas generating means contained and sealed within said lower chamber and within said annular ring and covered over by said inner body lower chamber such that as gas is generated said gas cannot escape from said lower chamber except through said gas exit port and into said upper chamber;
whereby as said reservoir cap is pressed downward, said lower chamber of said inner body seats around said annular ring causing said electro-chemical gas generating means to become activated generating gas into said upper chamber forcing fluid out of said bladder onto said pad.

19. The dispenser of claim 18 further comprising a seal over said fluid exit port.

20. The dispenser of claim 18 wherein said reservoir cap further comprises a centrally located spike under said head top and protruding downward and a plurality of support members under said head top around said spike.

21. The dispenser of claim 18 wherein said bladder is heat-sealed to said collar.

22. The dispenser of claim 18 wherein said collar and said bladder are comprised of a polyethylene composition with each having approximately identical softening temperatures to create an approximate leak-free air-tight seal between said collar and said bladder.

23. The dispenser of claim 18 further comprising an protruding ring on said head bottom and outward of said collar and a corresponding groove on the top of said inner body.

24. The dispenser of claim 23 wherein said head bottom is ultrasonically sealed to said top of said inner body after said protruding ring is seated into said corresponding groove.

25. The dispenser of claim 18 further comprising two outward extending wings on said pad wherein said wings are insertable into said side chambers.

26. The dispenser of claim 18 further comprising an air intake port within said annular ring.

27. The dispenser of claim 18 further comprising a fluid fill port through said head top and in communication with said bladder.

28. The dispenser of claim 18 further comprising an upstanding elongated tab on each side of said base housing, said elongated tabs having a width-W3.

29. The dispenser of claim 28 further comprising a registration slot on each side of said reservoir cap, said registrations slots have a width-W4 wherein said width-W4 is slightly greater than said width-W3 and adapted to retain and guide said elongated tabs which seat into said registration slots.

30. The dispenser of claim 28 further comprising an outward protruding stop on the distal end of each said elongated tab.

31. The dispenser of claim 30 further comprising an upper slot and a lower slot in each said registration slot adapted to receive and releasably retains said protruding stop.

32. The dispenser of claim 18 further comprising a side groove around said inner housing and a lock member adapted to removably insert through said cut-out and into said side groove to prevent said reservoir cap from translating downward until said lock member is removed from said side groove.

* * * * *